US012741076B2

(12) United States Patent
Schroeder

(10) Patent No.: US 12,741,076 B2
(45) Date of Patent: Sep. 22, 2026

(54) APPARATUS AND METHODS FOR PUNCTURING TISSUE AND REMOVING FLUIDS WITHOUT SPILLAGE

(71) Applicant: Grant Gregory Schroeder, Los Angeles, CA (US)

(72) Inventor: Grant Gregory Schroeder, Los Angeles, CA (US)

( * ) Notice: Subject to any disclaimer, the term of this patent is extended or adjusted under 35 U.S.C. 154(b) by 1177 days.

(21) Appl. No.: 17/674,649

(22) Filed: Feb. 17, 2022

(65) Prior Publication Data

US 2022/0265915 A1 Aug. 25, 2022

Related U.S. Application Data

(60) Provisional application No. 63/151,246, filed on Feb. 19, 2021.

(51) Int. Cl.
*A61M 1/00* (2006.01)
*A61B 17/34* (2006.01)
*A61F 2/958* (2013.01)

(52) U.S. Cl.
CPC ............... *A61M 1/76* (2021.05); *A61B 17/34* (2013.01); *A61F 2/958* (2013.01); *A61B 2017/3486* (2013.01)

(58) Field of Classification Search
CPC .... A61B 2017/3486; A61B 2017/3488; A61B 17/3415; A61B 2017/306; A61M 27/002; A61M 1/76; A61M 1/77; A61M 1/774; A61F 2/958
See application file for complete search history.

(56) References Cited

U.S. PATENT DOCUMENTS

| | | | | |
|---|---|---|---|---|
| 3,253,594 A * | 5/1966 | Matthews | ......... | A61M 39/0247 604/178 |
| 4,958,621 A | 9/1990 | Topel et al. | | |
| 5,882,331 A * | 3/1999 | Sasaki | .............. | A61B 17/00234 600/109 |
| 6,685,628 B2 | 2/2004 | Vu | | |
| 8,840,657 B2 | 9/2014 | Hartley | | |
| 9,974,530 B2 | 5/2018 | Smith et al. | | |
| 2006/0264966 A1 | 11/2006 | Armstrong | | |
| 2007/0239108 A1* | 10/2007 | Albrecht | ........... | A61M 39/0247 604/167.03 |

(Continued)

FOREIGN PATENT DOCUMENTS

| | | |
|---|---|---|
| WO | 1994015655 | 1/1994 |
| WO | 2006036938 A2 | 4/2006 |

*Primary Examiner* — Wesley G Harris
*Assistant Examiner* — Charles W Nichols
(74) *Attorney, Agent, or Firm* — GATES & COOPER LLP

(57) ABSTRACT

Aspects of the present disclosure relate to apparatuses and methods for puncturing a tissue wall (e.g., a tissue wall of a cancerous cyst) and removing fluids from the tissue without outward spillage of contents in vivo. In illustrative embodiments, the invention comprises the use of an apparatus disclosed herein including the steps of fixing an outer housing of the apparatus to the tissue wall with an adhesive, puncturing the tissue wall from within the outer housing so that any spillage is contained while reinforcing fixation to the tissue wall with a reinforcing element such as a balloon. In this way, the apparatuses and methods disclosed herein allow for spillage free tissue puncture and fluid collection.

14 Claims, 14 Drawing Sheets

(56) References Cited

U.S. PATENT DOCUMENTS

| | | | | |
|---|---|---|---|---|
| 2008/0171989 | A1* | 7/2008 | Bell | A61M 25/0662<br>604/170.01 |
| 2008/0200933 | A1 | 8/2008 | Bakos et al. | |
| 2008/0200934 | A1 | 8/2008 | Fox | |
| 2008/0287973 | A1* | 11/2008 | Aster | A61B 17/3421<br>606/153 |
| 2015/0126906 | A1 | 5/2015 | Kalloo et al. | |
| 2018/0008250 | A1 | 1/2018 | Joseph | |

* cited by examiner

APPARATUS AND METHODS FOR PUNCTURING TISSUE AND REMOVING FLUIDS WITHOUT SPILLAGE

CROSS REFERENCE TO RELATED APPLICATIONS

This application claims the benefit under 35 U.S.C. Section 119(e) of co-pending U.S. Provisional Patent Application Ser. No. 63/151,246 filed on Feb. 19, 2021 and entitled "APPARATUS AND METHODS FOR PUNCTURING TISSUE AND REMOVING FLUIDS WITHOUT SPILLAGE" which application is incorporated by reference herein.

TECHNICAL FIELD

The present invention is in the field of surgical procedure. More specifically, the invention provides apparatuses and methods that allow for the drainage of fluids from tissues including cysts and cyst-like structures while inhibiting spillage of such fluids into an in vivo environment.

BACKGROUND OF THE INVENTION

During surgery, a surgeon may be met with the problem of needing to extract a cyst or cyst-like structure without spilling the contents inside the structure into another cavity in vivo. For example, during the surgical removal of an ovarian cyst, a surgeon will attempt to extract the cyst without spillage of the internal fluid to avoid potential complications such as chemical peritonitis, gliomatosis peritonei, pseudomyxoma peritonei, cyst recurrence, and perhaps most notably, dissemination of cancerous cells if the cyst is malignant. Other examples where spillage avoidance is desired includes laparoscopic cholecystectomies and surgical management of hydatid cysts.

In ovarian cyst removal, surgeons typically attempt to employ oncological techniques to avoid cyst content spillage. Such techniques include carefully detaching the cyst from surrounding structures, placing it within an impermeable bag, bringing the ends of the bag outside of the body, puncturing the cyst once it is safely contained, and finally drawing the bag containing the decompressed cyst outside of the body. Alternatively, a surgeon may make a larger incision to allow for the mobilized cyst to be removed from the body intact. Sometimes however, the ability to carry out these oncological techniques is complicated by, for example, extremely large cysts, difficult to access cysts, thin-walled cysts, or cysts that are significantly adhered to neighboring structures, which increase the likelihood of inadvertent cyst puncture and content spillage into a body cavity.

With extremely large ovarian cysts, for which a surgeon would ordinarily have to make a large incision to safely remove, several case reports and case series have demonstrated the success of a technique whereby the cyst may be safely removed through a smaller incision. In this technique, a portion of an impermeable sheet or bag is adhered to a portion of the ovarian cyst through a small open incision with the aid of a surgical adhesive, usually a cyanoacrylate glue. The adhered portion can then be punctured, and the cyst can be decompressed with any cyst fluid spillage being contained exteriorly by the impermeable sheet or bag. This technique is limited by only being applicable to large and easily accessible cysts however, because the surgeon must be able to have adequate access to the cyst surface though an open incision. Consequently, such techniques cannot be employed laparoscopically, for example.

The ability to decompress a cyst without content spillage minimally invasively, such as during laparoscopy, represents an unmet clinical need. While several laparoscopic devices and instruments have attempted to limit cyst spillage upon puncture; they do not entirely prevent all spillage. For example, the commercially available double balloon catheters, which "sandwich" a tissue wall after puncture, have been shown to reduce gross spillage of contents in surgeries for ovarian cysts, hydrosalpinx, and acute cholecystitis. Additionally, the commercially available Topel Endoscopic Cyst Aspirator from Cook Medical reduces gross spillage of cyst contents by applying suction through an outer housing during puncture by a coaxial aspiration needle. In both of these examples, gross spillage of cyst contents can be reduced, however they are not intended to completely prevent all spillage. For example, for double balloon catheters, there is unavoidably some cyst fluid spillage during bare puncture before the internal balloon is inflated. For the Topel Aspirator, as soon as the outer housing supplying suction loses contact with the cyst surface, spillage may occur from the puncture site.

A reliable way to decompress a cyst without any spillage in a minimally invasive manner has largely remained elusive. Prior art devices and methods attempt to prevent any spillage of cyst contents by employing a technique akin to adhering a containment means to the cyst surface prior to puncture as previously described for open surgery, except the method is carried out with elongated instruments for laparoscopic surgery. In essence, this method adheres the distal end of a device having an elongated member comprising a lumen to a cyst tissue surface, before puncturing the cyst from within the lumen so that any spillage is contained. The method is limited however by the reliability of the distal end adhesion to the tissue. While adhesion in such prior art techniques may be initially appropriate, subsequent movements and manipulations during a procedure may lead to adhesive peeling, device detachment, and content leakage. These limitations have prevented such methods from being broadly utilized.

Thus, there currently remains a need for simplified devices and improved methods for the minimally invasive decompression of cysts or cyst-like structures without spillage of their contents.

SUMMARY OF THE INVENTION

As noted above, during the surgical resection of cysts or cyst-like structures, it can be of utmost importance for medical personnel including surgeons to remove these in vivo structures without spilling their internal contents in order to avoid an array of serious complications—most notably the dissemination of cancerous cells from malignant cysts. Current methods to prevent cyst spillage typically depend on a surgeon's ability to meticulously detach a cyst or cyst-like structure from surrounding tissue structures, and either remove the structure intact through a large incision or place it within a containment bag prior to puncture. A problem with these methods that large and/or significantly adherent cysts are often inadvertently punctured, spilling their contents during the process of manipulating and detaching them from surrounding structures. The present invention is designed to overcome such problems by allowing cysts and cyst-like structures to be punctured and drained while inside the body, a procedure which thereby provides for easier cyst detachment and extraction through smaller incisions, while simultaneously inhibiting or preventing spillage of cyst contents (e.g., cancerous cells). In this context, the apparatuses and methods disclosed herein can not only be used to expand the number of surgeries that may be accomplished using minimally invasive techniques, but can further increase the safety of cyst extractions by avoiding inadvertent spillage of cyst contents. In this way, embodiments of the present invention have widespread applications in the field of surgery, for example in the resection of both benign and malignant cysts and cyst-like structures.

The apparatuses and methods of the present invention are designed to allow the puncture of a tissue wall of cysts and cyst-like structures while simultaneously inhibiting the spillage of their contents from a puncture site. This can be accomplished, for example, by using an apparatus disclosed herein in an in vivo procedure where a portion/element of the apparatus is affixed and supported/reinforced on a cyst tissue surface with, for example, an adhesive, before puncturing the cyst tissue wall using a piecing member coupled to a fluid removal conduit that is disposed within a lumen of the apparatus, so that spillage from cysts and cyst-like structures is contained. In this context, a key aspect of the invention is a constellation of elements disposed on the apparatus that is designed to reinforce the fixation of the tissue contacting element of the apparatus to a cyst tissue wall in order to prevent detachment, as can occur with certain apparatuses/devices previously described in this art. As discussed in detail below, this is accomplished by using an apparatus having a constellation of elements that includes a reinforcing member that is designed to provide a backing/matrix structure that supports the tissue to which the tissue contacting element of the apparatus is attached. In typical embodiments of the invention, the reinforcing member is an activatable reinforcing member, such as a balloon that is inflated in vivo in order to provide support for the portion of the apparatus that is affixed to the tissue.

The invention disclosed herein has a number of embodiments. Embodiments of the invention include, for example, an apparatus such as a medical device comprising: an outer housing defining a lumen comprising a proximal portion and a distal portion; a tissue contacting element in operable contact with the distal portion of the outer housing and comprising a surface adapted to adhere to tissue forming a surface of a tissue such as a cyst; an elongate assembly disposed within the outer housing comprising: a proximal portion; a distal portion; and an activatable tissue reinforcing element. In this embodiment, elements including the tissue contacting element and the activatable tissue reinforcing element are disposed in an arrangement on the device such that: the outer housing can be inserted in a patient in vivo so that the tissue contacting element is adhered to the outer surface tissue of the cyst; the activatable tissue reinforcing element can be activated so as to provide a support for the tissue contacting element adhering to an outer surface of the cyst; and a piercing member operably connected to the elongate assembly can be advanced through the lumen and puncture the cyst; such that fluid can be removed from the cyst as the activatable tissue reinforcing element provides support for the tissue contacting element adhering to an outer surface of the cyst; thereby inhibiting leakage of fluid from the cyst in vivo.

In certain embodiments of this medical device, the activatable tissue reinforcing element comprises an inflatable balloon; the lumen comprises a conduit for a gas or a liquid; and the conduit is operably connected to a port that introduces a gas or fluid into the balloon. Optionally such devices further comprise an adhesive applicator disposed on the device to apply an adhesive to the tissue contacting element. In certain embodiments of the invention, the devices further comprise a drying element disposed on the device to remove liquid from the outer surface tissue of a cyst prior to adhering the tissue contacting element to the outer surface tissue of a cyst. Typically, the device further comprises a securing mechanism that operably connects the outer housing to the elongate assembly.

Embodiments of the invention further include methods of removing fluids from a tissue structure (e.g. a cyst) in a manner that inhibits in vivo spillage of such fluids from the tissue structure. For example, embodiments of the invention include methods for removing fluid from a cyst or cyst like structure using an apparatus/device as disclosed herein. Typically these methods include manipulating the device so that the outer housing defining the lumen is disposed in an in vivo location in a patient having the cyst or cyst like structure; affixing a tissue contacting element to a tissue wall of the cyst or cyst like structure using an adhesive; activating an activatable tissue reinforcing element; puncturing the tissue wall of the cyst or cyst like structure; and then removing the fluid through the puncture via a fluid conduit that is disposed within the lumen formed by the outer housing of apparatuses/devices disclosed herein.

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

Referring now to the drawings in which like reference numbers represent corresponding parts throughout.

DETAILED DESCRIPTION OF THE INVENTION

In the description of embodiments, reference may be made to the accompanying figures which form a part hereof, and in which is shown by way of illustration a specific embodiment in which the invention may be practiced. It is to be understood that other embodiments may be utilized, and structural changes may be made without departing from the scope of the present invention. Embodiments of the present invention, including the illustrative embodiment, will now be described while referencing the drawings. The same reference numbers will be used in all drawings whenever possible.

Related art that illustrates this type of technology includes the following publications: U.S. Pat. Nos. 4,958,621, 5,882,331, 6,685,628, 8,840,657 and 9,974,530; U.S. Patent Application Publication Nos. 2006/0264966, 2008/0200934, 2008/0200933, 2008/0171989, 2015/0126906 and 2018/0008250; and PCT Publication Nos. WO 94/15655 and WO 2006/036938. All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

Figure 1:
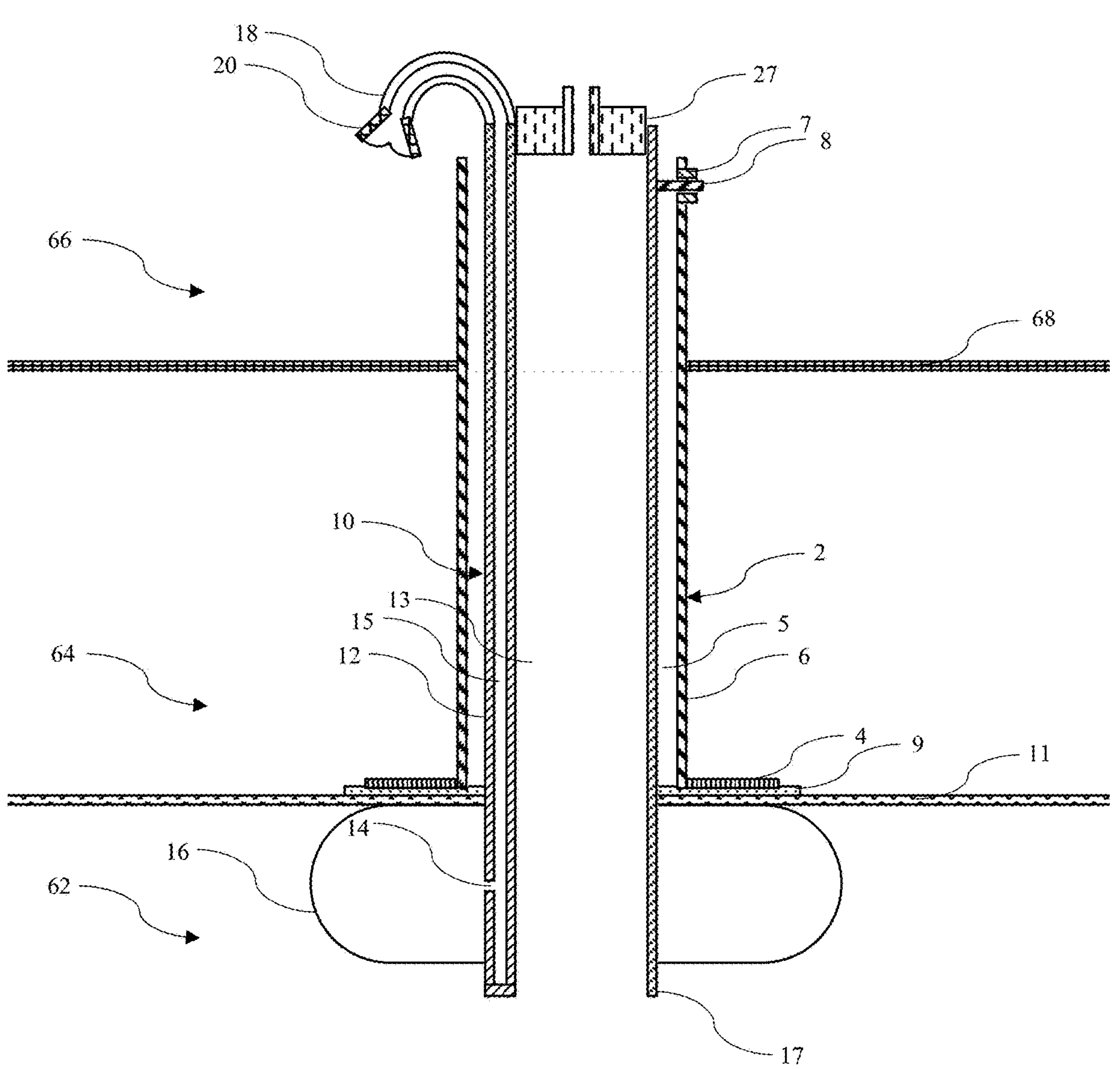
FIG. 1 depicts a sectional view of the principal components of an exemplary embodiment of the invention in its working state.
Figure 2:
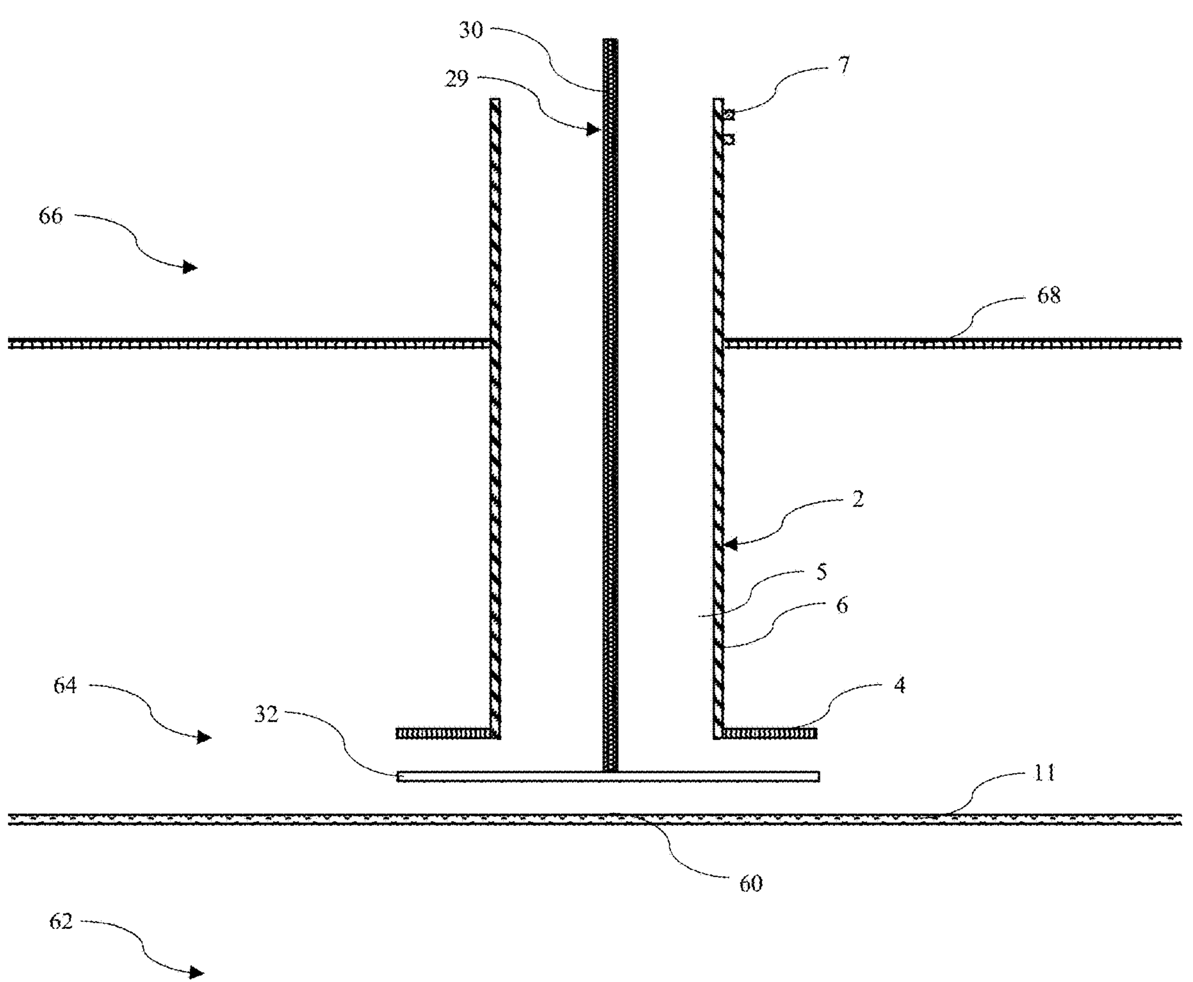
FIG. 2 depicts a sectional view of an exemplary embodiment of the invention involving drying the tissue wall.
Figure 4:
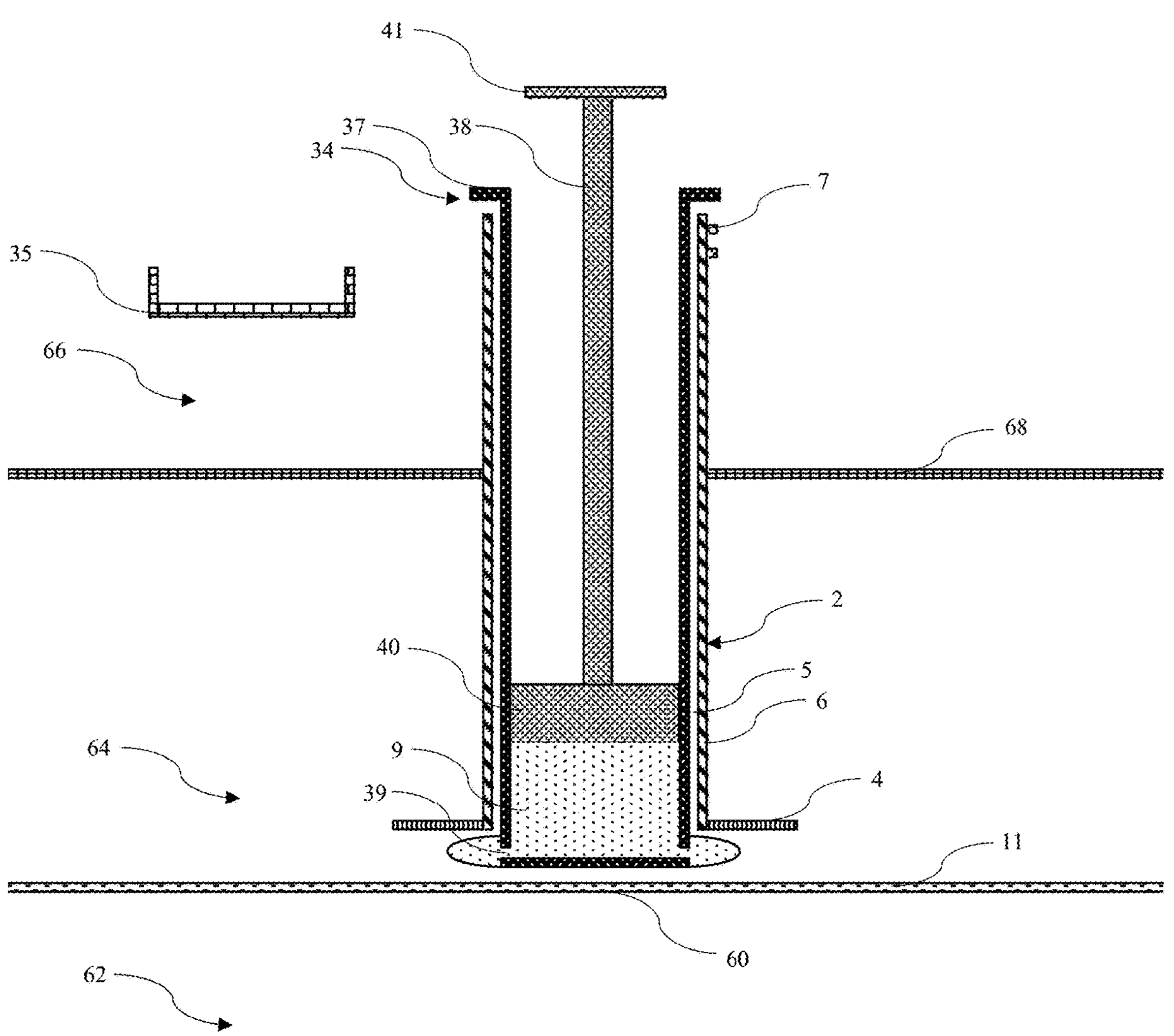
FIG. 4 depicts a sectional view of an exemplary embodiment of the invention involving applying adhesive to the tissue wall.
Figure 5:
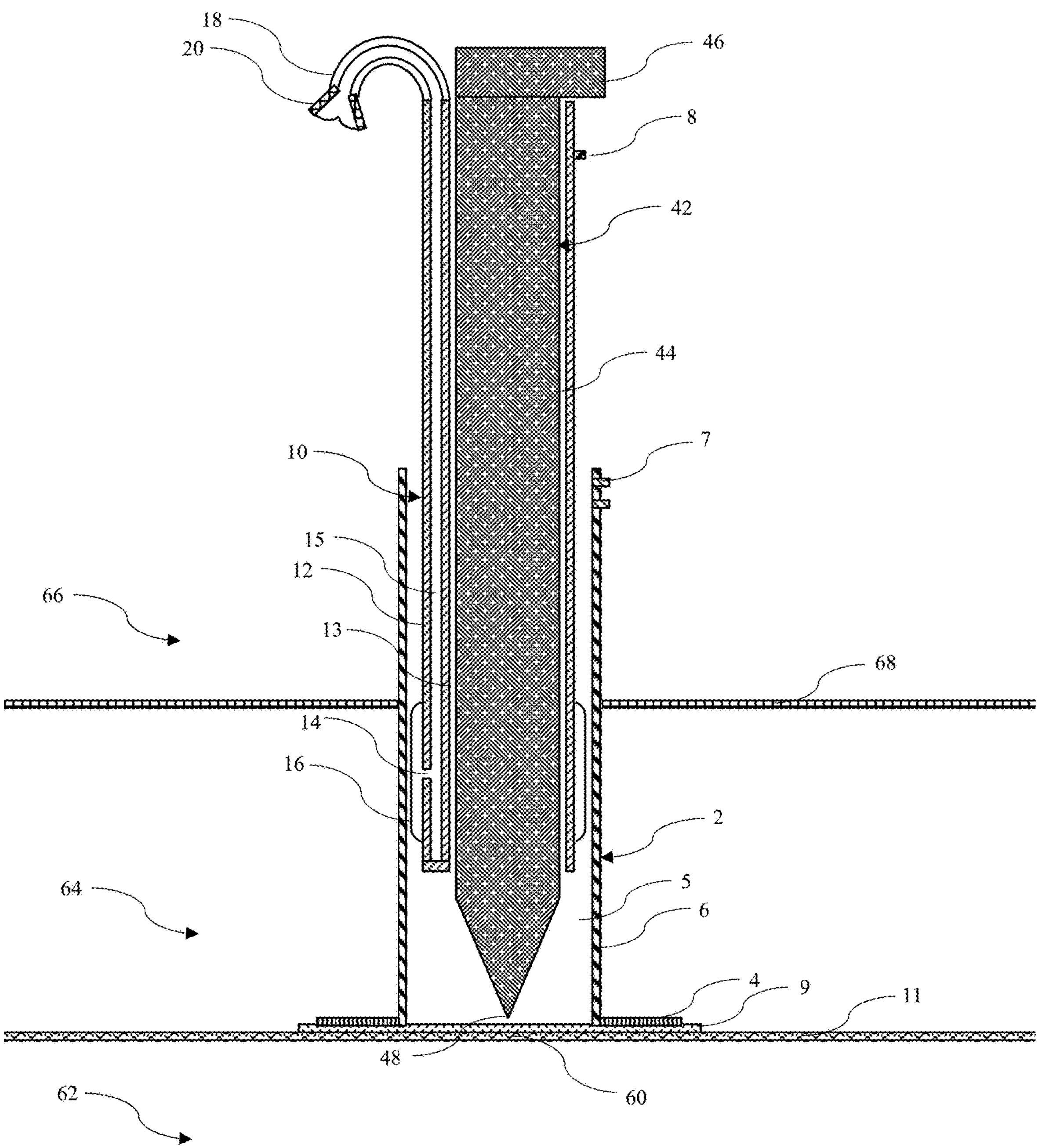
FIG. 5 depicts a sectional view of an exemplary embodiment of the invention involving advancing the elongate assembly and the piercing member in the lumen of the outer housing.

The invention disclosed herein has a number of embodiments. Embodiments of the invention include, for example, an apparatus for puncturing a tissue wall, the apparatus comprising an outer housing (e.g., element 2 as shown in FIG. 1) defining a lumen (e.g., element 5 as shown in FIG. 1) having a proximal portion, a distal portion, and a tissue contacting element (e.g., element 4 as shown in FIG. 1) and an elongate assembly (e.g., element 10 as shown in FIG. 1) having a proximal portion, a distal portion, and an activatable tissue reinforcing element (e.g. an inflatable balloon) (e.g., element 16 as shown in FIG. 1). In such embodiments, the elements are disposed in a three-dimensional architectural configuration on the apparatus designed so that: the outer housing can be advanced through a proximal space, for example an in vivo body cavity such as a one created by insufflation with a gas (e.g., element 64 as shown in FIG. 1); the tissue contacting element can be fixed to a tissue wall (e.g., element 11 as shown in FIG. 1); the elongate assembly can be advanced through the lumen and is distal portion into a distal space, for example an internal region of a cyst or cyst like structure that occurs in vivo (e.g., element 62 as shown in FIG. 1) through a puncture in the tissue wall; and the activatable tissue reinforcing element can be activated within the distal space. In certain embodiments of the invention, the apparatus includes a drying element (e.g., element 29 as shown in FIG. 2) that can be used to dry the tissue wall prior to fixing the distal portion of the outer housing to the tissue wall. In certain embodiments of the invention, the apparatus includes an adhesive applicator (e.g., element 34 as shown in FIG. 4) that can apply an adhesive (e.g., element 9 as shown in FIG. 4) for fixation of the distal portion of the outer housing to the tissue wall. Typically, the apparatus further comprises a piercing member (e.g., element 42 as shown in FIG. 5) that can form a puncture in the tissue wall from within the lumen formed by the outer housing. In some embodiments of the invention, the apparatus further includes a suction device and fluid conduit that can be attached to the elongate assembly for removing material from the distal space (e.g. removing cyst fluids/materials in vivo) through this lumen.

Figure 11:
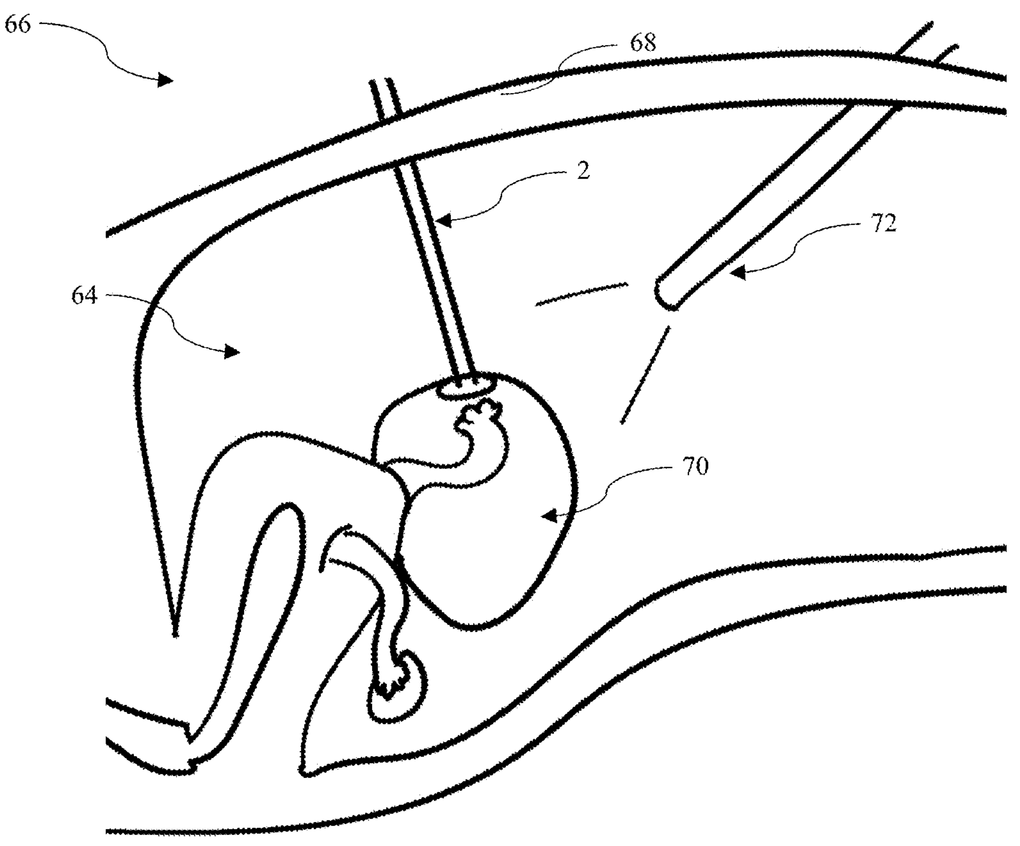
FIG. 11 depicts a compositional view of an exemplary embodiment of the invention involving laparoscopic surgery.

Closely related embodiments of the invention include medical devices comprising: an outer housing defining a lumen and comprising a proximal portion and a distal portion; a tissue contacting element in operable contact with the distal portion of the outer housing and comprising a surface adapted to adhere to a tissue wall forming a surface of a cyst or cyst-like structure (e.g., element 70 as shown in FIG. 11); an elongate disposed within the outer housing comprising: a proximal portion; a distal portion; and an activatable tissue reinforcing element. In such embodiments, the tissue contacting element and the activatable tissue reinforcing element are disposed in an arrangement on the device such that: the outer housing can be inserted in a patient in vivo so that the tissue contacting element is adhered to the outer surface tissue of the cyst; a piercing member operably connected to the elongate assembly can be advanced through the lumen and puncture the cyst or cyst-like structure; the activatable tissue reinforcing element can be activated so as to provide a support for the tissue contacting element adhering to an outer surface of the cyst or cyst-like structure; and fluid can be removed from the cyst or cyst-like structure via a fluid conduit within the lumen as the activatable tissue reinforcing element provides support for the tissue contacting element adhering to an outer surface of the cyst or cyst-like structure; thereby inhibiting leakage of fluid from the cyst or cyst-like structure in vivo.

In certain embodiments of this medical device, the activatable tissue reinforcing element comprises an inflatable balloon; the lumen comprises a conduit for a gas or a liquid (e.g., element 15 as shown in FIG. 1); and the conduit is operably connected to a port/opening (e.g., element 14 as shown in FIG. 1) that introduces a gas or fluid into the balloon. Optionally such devices further comprise an adhesive applicator disposed on the device to apply an adhesive to the tissue contacting element. In certain embodiments of the invention, the device further comprises a drying element disposed on the device to remove liquid from the outer surface tissue of a cyst or cyst-like structure prior to adhering the tissue contacting element to the outer surface tissue of a cyst or cyst-like structure. Typically, the device further comprises a securing mechanism that operably connects the outer housing to the elongate assembly (e.g., elements 7 and 8 as shown in FIG. 1).

One illustrative embodiment of the invention is an apparatus comprising an outer housing comprising a proximal portion, a distal portion and a lumen; a tissue contacting element in operable contact with the distal portion of the outer housing and comprising a surface adapted to adhere to tissue forming a surface of a cyst or cyst-like structure; an elongate assembly disposed within the outer housing comprising: a proximal portion; a distal portion; and an activatable tissue reinforcing element. In this embodiment, the tissue contacting element and the activatable tissue reinforcing element are disposed in an arrangement on the apparatus such that: the outer housing can be inserted in a patient in vivo so that the tissue contacting element is adhered to the outer surface tissue of the cyst or cyst-like structure and the distal portion of the elongate assembly can be advanced through a puncture in the wall of the cyst or cyst-like structure; the activatable tissue reinforcing element is disposed in the apparatus so as to provide a support for the tissue contacting element adhering to an outer surface of the cyst or cyst-like structure; and the apparatus can be disposed in vivo so that fluid can be removed from the cyst or cyst-like structure through the lumen, thereby inhibiting leakage of fluid from the cyst or cyst-like structure in vivo. In this context, the activatable tissue reinforcing element (for example, a balloon) is activated in the distal space once a puncture is formed on the cyst or cyst-like structure. Typically, the steps for doing so are: 1) adhere the outer housing to the cyst or cyst-like structure; 2) advance the elongate assembly though outer housing; 3) form a puncture in the cyst; and then 4) activate tissue reinforcing element (e.g., inflating the balloon).

Embodiments of the invention further include methods of removing fluids from a tissue structure (e.g., a cyst) in a manner that inhibits in vivo spillage of such fluids from the tissue structure. For example, embodiments of the invention include methods for removing fluid from a cyst or cyst-like structure with an apparatus/device as disclosed herein. Typically, these methods include manipulating the device so that the outer housing defining the lumen is disposed in an in vivo location in a patient having the cyst or cyst like structure; affixing the tissue contacting element to a tissue wall of the cyst or cyst like structure using an adhesive; puncturing the tissue wall of the cyst or cyst like structure; activating the activatable tissue reinforcing element; and removing fluid from the cyst or cyst like structure.

Embodiments of the invention include, for example, methods for puncturing a tissue with an apparatus/device disclosed herein, for example one comprising an outer housing comprising a proximal portion and a distal portion and a lumen. Such devices include an elongate assembly disposed within the lumen, the elongate assembly comprising a proximal portion, a distal portion; and an activatable tissue reinforcing element. In typical embodiments, the methods include advancing the outer housing comprising a lumen through a proximal space; contacting the distal portion of the outer housing to a tissue; advancing the elongate assembly through the lumen; puncturing the tissue from within the lumen of the device; and activating the activatable tissue reinforcing element from within a distal space so that the tissue is in operable contact with the activatable tissue reinforcing element, thereby limiting mobility of the tissue.

Embodiments of the invention also include, for example, methods for puncturing a tissue wall (e.g., the wall of a cyst or cyst like structure) with an instrument/device having an outer housing defining a lumen having a proximal portion and a distal portion and an elongate assembly having a proximal portion, a distal portion, and an activatable tissue reinforcing element. Typically, these methods comprise: advancing the outer housing defining a lumen through a proximal space; fixing the distal portion of the outer housing to a tissue wall; advancing the elongate assembly through the lumen; forming a puncture in the tissue wall from within the lumen to a distal space; and activating the activatable tissue reinforcing element from within the distal space. In certain embodiments of the invention, the methods further comprise drying the tissue wall prior to fixing the distal portion of the outer housing to the tissue wall. Optionally, the distal portion of the outer housing is fixed to the tissue wall with an adhesive. As an alternative to an adhesive (or in combination with an adhesive), the distal portion of the outer housing is fixed to the tissue wall via an alternative method or element such as the use of suction or cauterization. In some embodiments of the invention, the methods further include fixing the outer housing and the elongate assembly in relation to each other with a securing mechanism. In some embodiments of the invention, the methods further include adding and/or removing material into/out of the distal space through the at least one lumen within the elongate assembly. Optionally the methods comprise inserting at least one surgical instrument through at least one lumen within the elongate assembly.

As disclosed herein, an objective of the present invention is to allow for the puncture of a tissue wall without any spillage of contents in vivo from a space distal to the puncture site. This can be accomplished using a device/apparatus and/or method disclosed herein and by advancing an outer housing of the device/apparatus and fixing it to the tissue wall with, for example, an adhesive, before puncturing the tissue wall from within the outer housing so that any spillage is contained. A second objective of the present invention is to reinforce the fixation of the outer housing to the tissue wall after puncture to prevent initial fixation failure. This may be accomplished as disclosed herein, for example by activating a reinforcing member, such as a balloon, from a space distal to the puncture site. Further illustrative embodiments of the invention are described in the flowing text and associated figures.

FIG. 1 shows the principal components of one illustrative embodiment of the invention, components comprising an outer housing 2, adhesive 9, and elongate assembly 10. In this embodiment, the outer housing 2 can be advanced from an outside space 66, through a body wall (e.g., skin) 68, and through a proximal space 64. The outer housing 2 can then be fixed to a tissue wall 11, via a fixing element such as the adhesive 9, which for example could be a cyanoacrylate adhesive or the like. The surface area of interaction between the distal end of the outer housing 2 and the tissue wall 11 can be increased by a tissue contacting element 4, which can be composed of a flexible material such as rubber or the like. An elongated tubular body 6 of the outer housing 2 can be composed of a rigid material such as plastic or metal or the like, or a flexible material such as rubber or the like, or a combination of flexible and rigid components. At the proximal end of the outer housing 2 can be a securing mechanism 7 that can interact with a securing mechanism 8 of the elongate assembly 10 to secure the outer housing 2 to the elongate assembly 10. The tubular body 12 of elongated assembly 10 can be composed of a rigid material such as plastic or metal or the like, or a flexible material such as rubber or the like, or a combination of flexible and rigid components The elongate assembly 10 can pass through the lumen 5 of the outer housing, and puncture the tissue wall 11, such that there becomes at least a small continuity between a distal space 62 and the lumen 5, but no such continuity between the distal space 62 and a proximal space 64. Parts of outer housing 2 and elongate assembly 10 can be integrally molded or separate parts can be manufactured and then assembled. Near a distal portion 17 of the elongate assembly 10 can be an activatable tissue reinforcing element 16 which can be reversibly activatable, such as an inflatable balloon made of polyester, nylon, polyurethane, silicone, or the like. The activatable tissue reinforcing element 16 can be a balloon that is reversibly expandable via an inflation opening 14 that is continuous with a lumen 15 of the elongate assembly 10, which can be a conduit for gas or liquid to expand the balloon. Gas or liquid can be introduced via an inflation adapter 20 that can be connected to the lumen 15 via a flexible tubular body 18. At the proximal end of the elongate assembly 10 can be a connector 27 that is capable of connecting a lumen 13 to other items such as suction tubing arising from a suction device. The connecter 27 can be removable to allow wider access to lumen 13. The activatable tissue reinforcing element 16 can be held in relation to the outer housing 2 by way of securing mechanism 7 and securing mechanism 8, such that a seal is formed which would prevent fluid spillage from the distal space 62 into the proximal space 64 in the event adhesive 9 seal failure.

Figure 12:
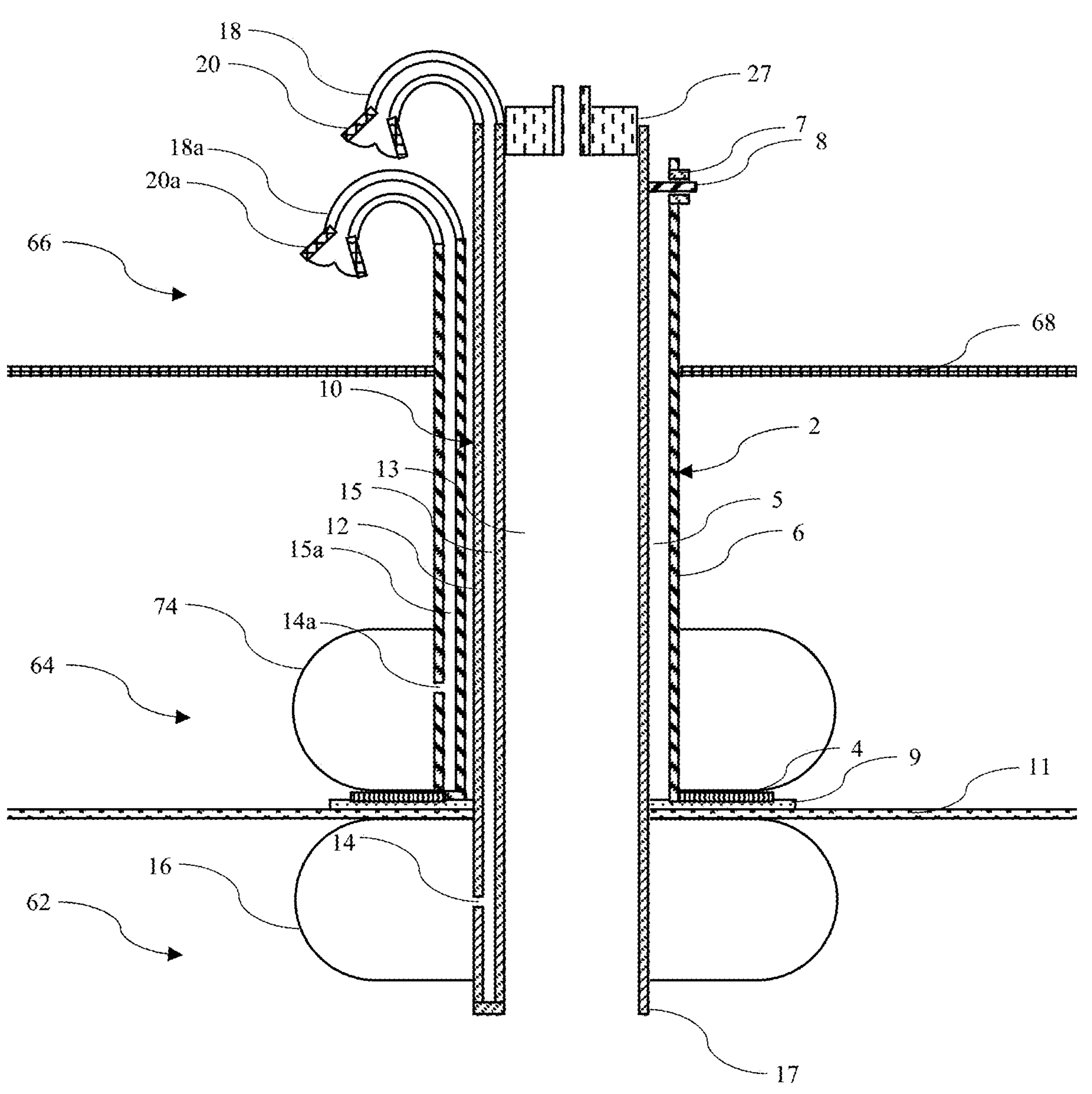
FIG. 12 depicts a sectional view of an exemplary embodiment of the invention involving activating a second tissue reinforcing element proximal to the tissue wall.
Figure 13:
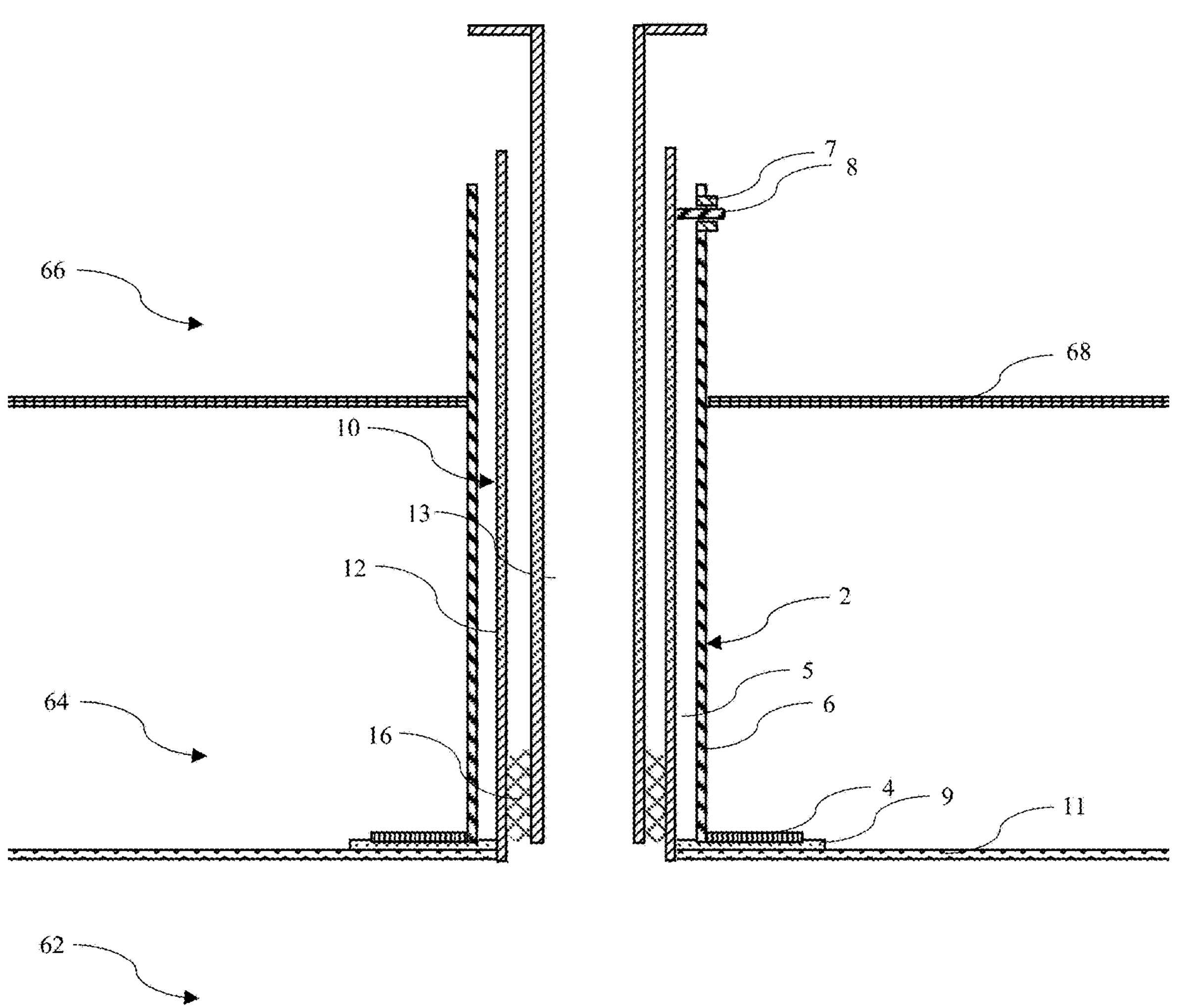
FIG. 13 depicts a sectional view of an exemplary embodiment of the invention involving advancing the activatable tissue reinforcing element through the lumen of the outer housing.
Figure 14:
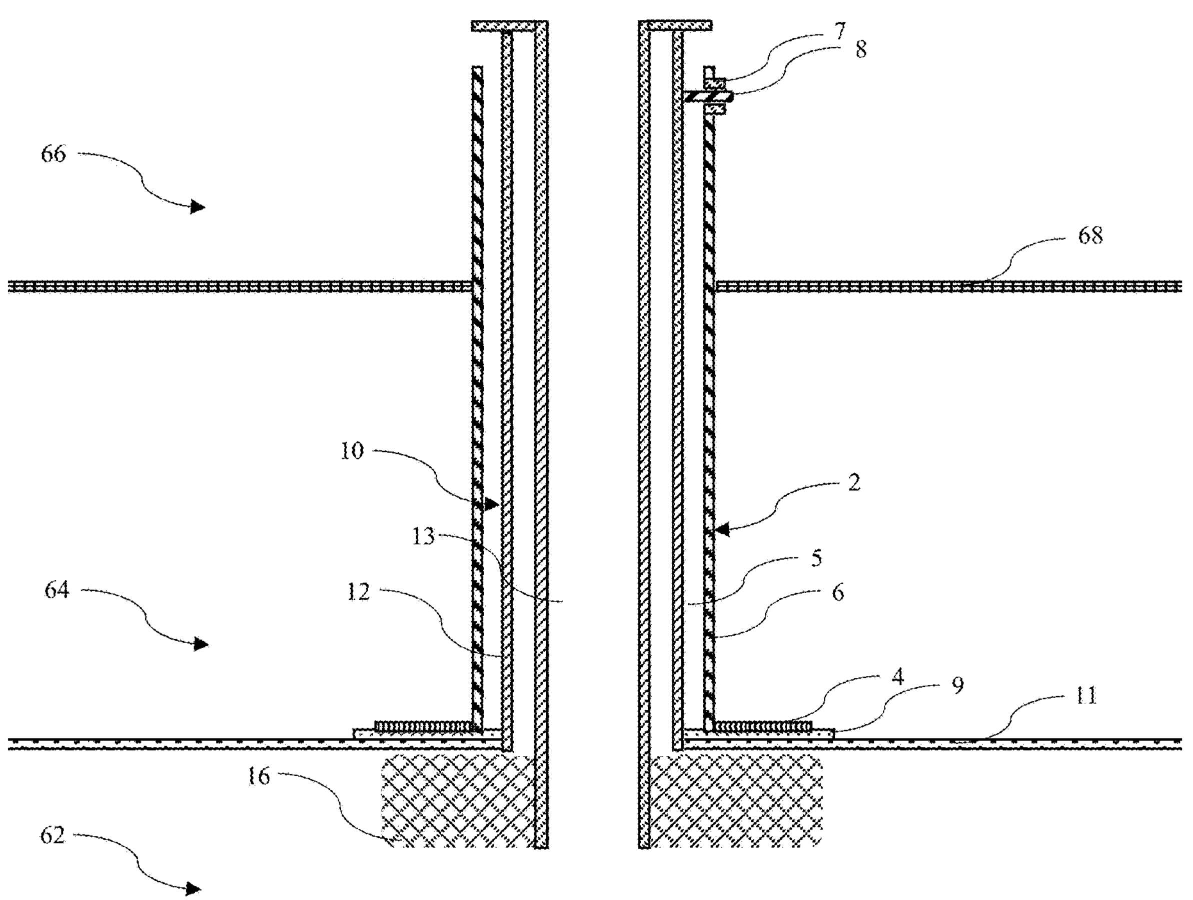
FIG. 14 depicts a sectional view of an exemplary embodiment of the invention involving activating the activatable tissue reinforcing element—in this embodiment, a stent/cage—in the distal space.

In alternative embodiments, the outer housing 2 can be fixed to the tissue wall 11 via an element other than an adhesive, including but not limited to suction, downward pressure, thermoplastic adhesive bonding, ultraviolet curing, tissue grasping, and/or cauterization. In another embodiment the outer housing 2 does not comprise tissue contacting element 4, or can comprise an alternative element such as a dome-shaped object. Alternatively, outer housing 2 can resemble an elongated bag that is open at its proximal end and closed at its distal end. In other alternative embodiments, the activatable tissue reinforcing element 16 is not a balloon, but the purpose of the activatable tissue reinforcing element 16 in reinforcing the fixation of outer housing 2 to the tissue wall 11 can be accomplished with an object placed in the distal space 62 that is activatable or expandable such as a stent, cage—as shown in FIGS. 13 and 14—or scissor-like device like for example, forceps. In another embodiment, as shown in FIG. 12, a second tissue reinforcing element 74 disposed on the outer housing 2 can be configured to be activated and interact to form a seal with activatable tissue reinforcing element 16, such as for example, a two-balloon compressive interaction. In embodiments comprising a two-balloon compressive interaction, the second tissue reinforcing element 74 may be activated in a similar manner to a balloon disposed on the elongate assembly 10, with an inflation adapter **20*a*, flexible tubular body 18*a*, lumen 15*a*, and inflation opening 14*a*; or it may be activated in a number of other ways that are obvious to those with ordinary skill in the art of balloon catheter design. In yet another embodiment, magnetic attraction between the distal portion of outer housing 2 or a component of elongate assembly 10 and one or more objects introduced into the distal space 62 such as magnetic beads can accomplish the reinforcing objective. In embodiments involving a balloon for the activatable tissue reinforcing element 16, the element to inflate such a balloon are numerous and are obvious to one with ordinary skill in the art. In other embodiments, connector 27 can be permanently affixed to either the elongate assembly 10, other tubing such as suction tubing, both, or neither. In other embodiments, connector 27 can have various ports including but not limited to a suction port, tool insertion port, and irrigation port, which may allow simultaneous actions from within the lumen 13 at the same time. In other embodiments the securing of the outer housing 2 to the elongate assembly 10 can be accomplished in a variety of ways including but not limited to applying a clip to the elongate assembly 10, expanding a balloon on the proximal end of elongate member 10, closing a latch, or engaging a locking mechanism. In another embodiment outer housing 2 or elongate assembly 10** can be held in a fixed position via an attachment to a stationary object in the surgical field, allowing the user to release his or her hand grip.

Figure 3:
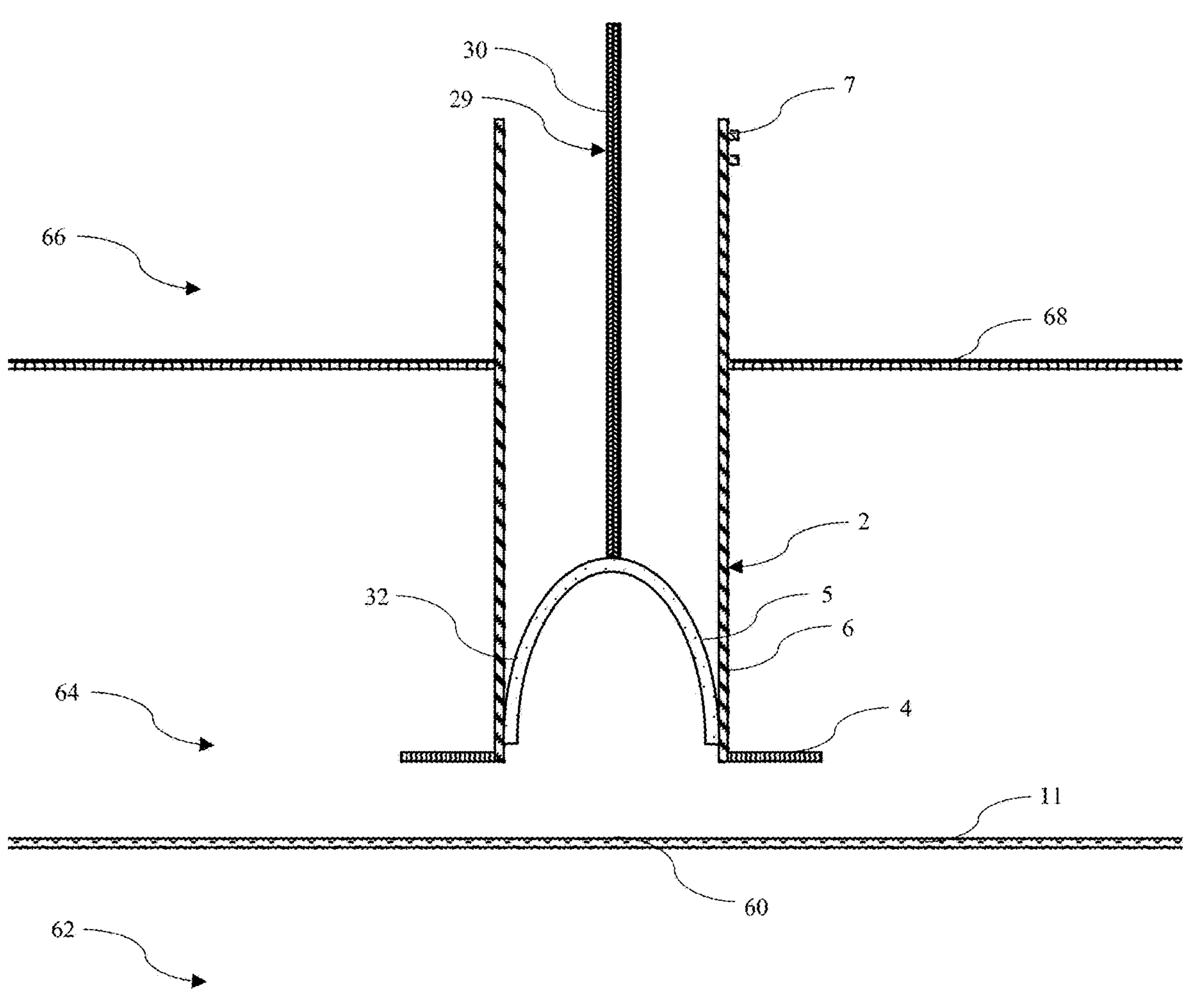
FIG. 3 depicts a sectional view of an exemplary embodiment of the invention involving removing the drying means.

FIGS. 2 and 3 show the illustrative embodiment of drying the working site 60 of the tissue wall 11. A drying element 29 is inserted into the outer housing 2 prior to advancing the outer housing 2 toward the working site 60. The drying element 29 can comprise an elongate member 30, which can be made of a rigid or semi-rigid material such as plastic or metal or the like, and a distal drying body 32, which can be made of an absorptive fabric or sponge, for example. Upon contacting the working site 60, the drying body 32 can absorb moisture from the surface of the tissue wall 11 and/or the tissue contacting element 4. The user can rotate the elongate member 30 at its proximal end or drag the drying element 29 across the working site 60 to enhance drying. The drying element 29 can be removed from the lumen 5 of the outer housing 2 owing to the conformability of the drying body 32.

In an alternative embodiment, the drying element 29 can be inserted through the outer housing 2 after the outer housing 2 has been advanced to the working site 60. Alternatively, the drying element 29 can be used and removed prior to advancing the outer housing 2 toward the working site 60. In another embodiment, the drying element 29 is introduced from an alternate site than the outer housing 2 and can dry the working site 60 and/or the tissue contacting element 4 before being extracted through said alternate site. In other embodiments the drying element 29 is attached to the outer housing 2 and is removable via retraction by pulling, for example, an attached elongated member held on the proximal part of the outer housing 2 or via another tool such as for example a grasper. In alternative embodiments, a drying element 29 can be a supplier of air or a drying liquid, or can provide suction, or can be a combination of any of these and/or a drying body 32, which can dry the working site 60. In other embodiments, no drying element 29 would be employed at all.

FIG. 4 shows the illustrative embodiment of adhesive application to the working site 60. An adhesive applicator 34 has its applicator cap 35 from its distal end removed. The adhesive applicator 34 is then advanced into the lumen 5 of the outer housing 2, until a syringe holder 37 makes contact with the proximal portion of outer housing 2. A user can then depress a plunger head 41, which is attached to a plunger disc 40 via a plunger neck 38, causing the adhesive 9 to be extruded from a one or more extrusion openings 39. Extrusion openings 39 can be configured to extrude the adhesive 9 circumferentially to preferentially apply the adhesive 9 laterally rather than in the center of the working site 60. The adhesive 9 can be a cyanoacrylate for example, which can have other components added to make it more gel-like and less likely to drip toward non-target sites. Following full depression of the plunger head 41 and the application of a preset amount of adhesive 9 which can be between 0.1 and 3 cc, the adhesive applicator 34 can be withdrawn from the outer housing 2. A user can then manipulate the outer housing 2 such as dabbing or sweeping the adhesive 9 or rotating the outer housing 2 to allow for the adhesive 9 to form a continuous ring on the tissue contacting element 4. The outer housing 2 can then be held in position with some pressure on the working site 60 for several seconds to minutes to allow the adhesive 9 to set. The seal formed by the adhesive 9 can be tested by various methods including but not limiting to putting traction on the tissue wall 11, visual inspection, filling liquid into lumen 5 and inspecting for leakage, or applying pressure within lumen 5 to assess if the seal is gas-tight.

In an alternative embodiment, the adhesive applicator 34 can be used to apply adhesive and removed prior to advancing the outer housing 2 toward the working site 60. Alternatively, the adhesive applicator 34 is introduced from an alternate site than the outer housing 2 and can be used to apply adhesive 9 on working site 60 or tissue contacting element 4 before being extracted through said alternate site. In other embodiments the adhesive applicator 34 is contained in a reservoir in outer housing 2 and is releasable for example by pulling a release mechanism, applying pressure to break the reservoir, or puncturing the reservoir with an elongated instrument. In another embodiment, the adhesive applicator 34 has two or more reservoirs with contents that form activated adhesive 9 upon mixing, such as when passing though mixing nozzle. In other embodiments, there can be a plurality of adhesive applicators dispensing the same or different substance onto the working site 60. In another embodiment, the adhesive 9 is already applied to tissue contacting element 4 and is exposed upon removing a covering, for example like a sticker. In another embodiment, adhesive 9 is activated by one or more activating elements, for example an ultraviolet light. In another embodiment, an adhesive containment system can be employed to prevent the migration of adhesive 9 to non-target sites, which can comprise a containment ring, shelf, or sheet that is part of the adhesive applicator 34, the outer housing 2, attachable to another surgical instrument, or exists as a standalone part.

Figure 6:
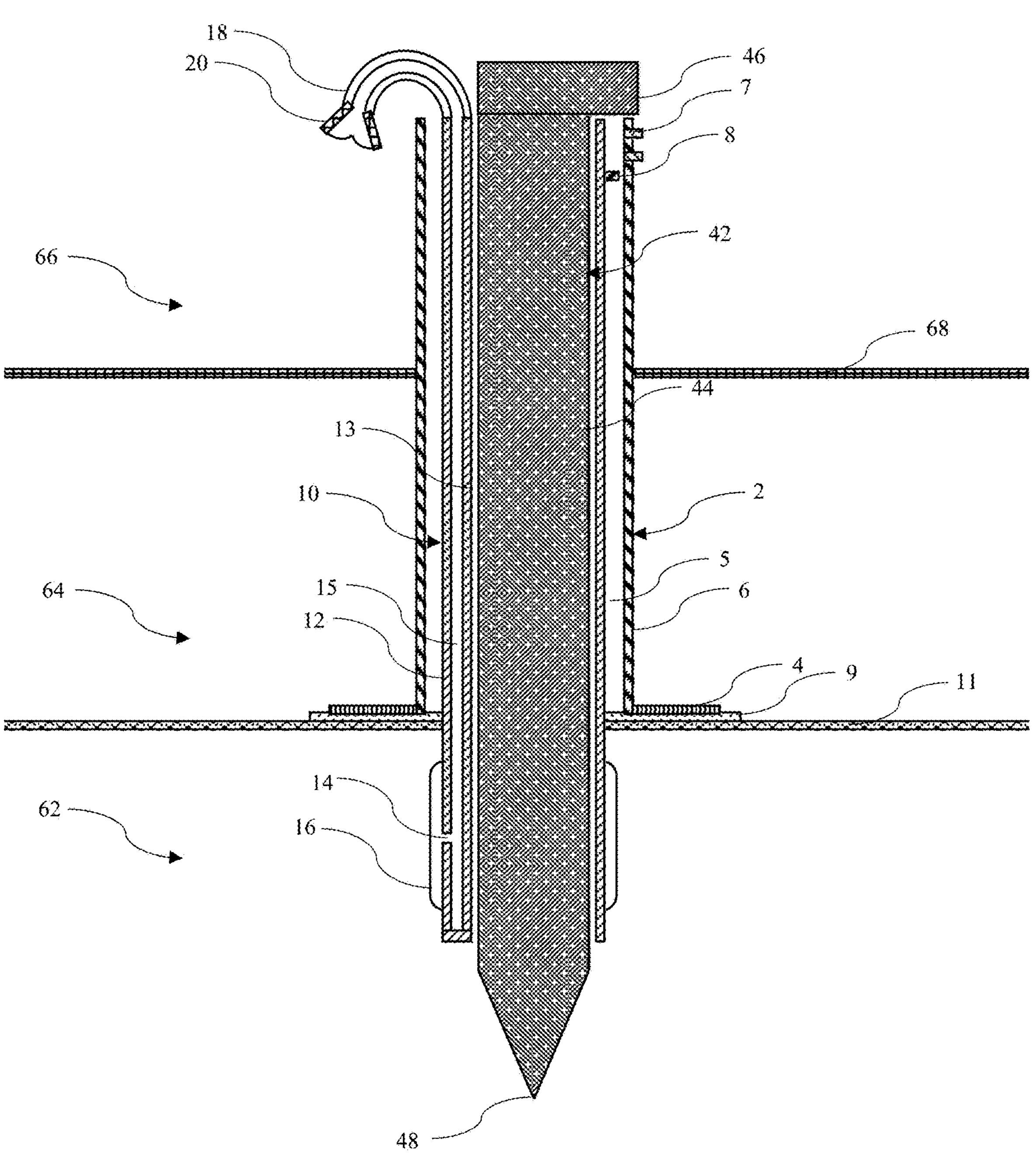
FIG. 6 depicts a sectional view of an exemplary embodiment of the invention involving puncturing the tissue wall.

FIGS. 5 and 6 shows the illustrative embodiment of puncturing the tissue wall 11. A piercing member 42, comprising a piercing member body 44, a piercing member holder 46, and a piercing member point 48, which can be made of plastic or metal or the like and can be rigid or semi-rigid, is inserted into the elongate assembly 10 before advancing the elongate assembly 10 into the lumen 5 of the outer housing 2. Distal advancement of the piercing member 42 and elongate assembly 10 results in the puncture of the tissue wall 11, and the formation of continuity between the distal space 62 and the lumen 5 of the outer housing 2 but no such continuity between the distal space 62 and the proximal space 64. Following puncture and advancement of the piercing member 42 and elongate assembly 10, the piercing member 42 can be removed from the elongate assembly 10.

In another embodiment a separate piercing member 42 would not be employed and the tissue wall 11 would simply be punctured by the distal portion of the elongate assembly 10, in this case making the elongate assembly 10 and the piercing member 42 one-in-the-same. In another embodiment a piercing member 42 would be used to puncture the tissue wall 11 and then extracted before advancing the elongate assembly 10 though the puncture site. In other embodiments, an elongated member that is rigid or semi-rigid can serve the same purpose of puncturing as the piercing member 42, but might not be strictly defined as a piercing member. In another embodiment, an elongate member can be inserted through the elongate assembly 10 for the purpose of preventing non-hardened adhesive 9 from migrating into lumen 13 during puncture. In yet another embodiment, an elongated member can be inserted into lumen 5 and used to extract excess non-hardened adhesive from the working site 60, either before or after inserting elongate assembly 10.

Figure 7:
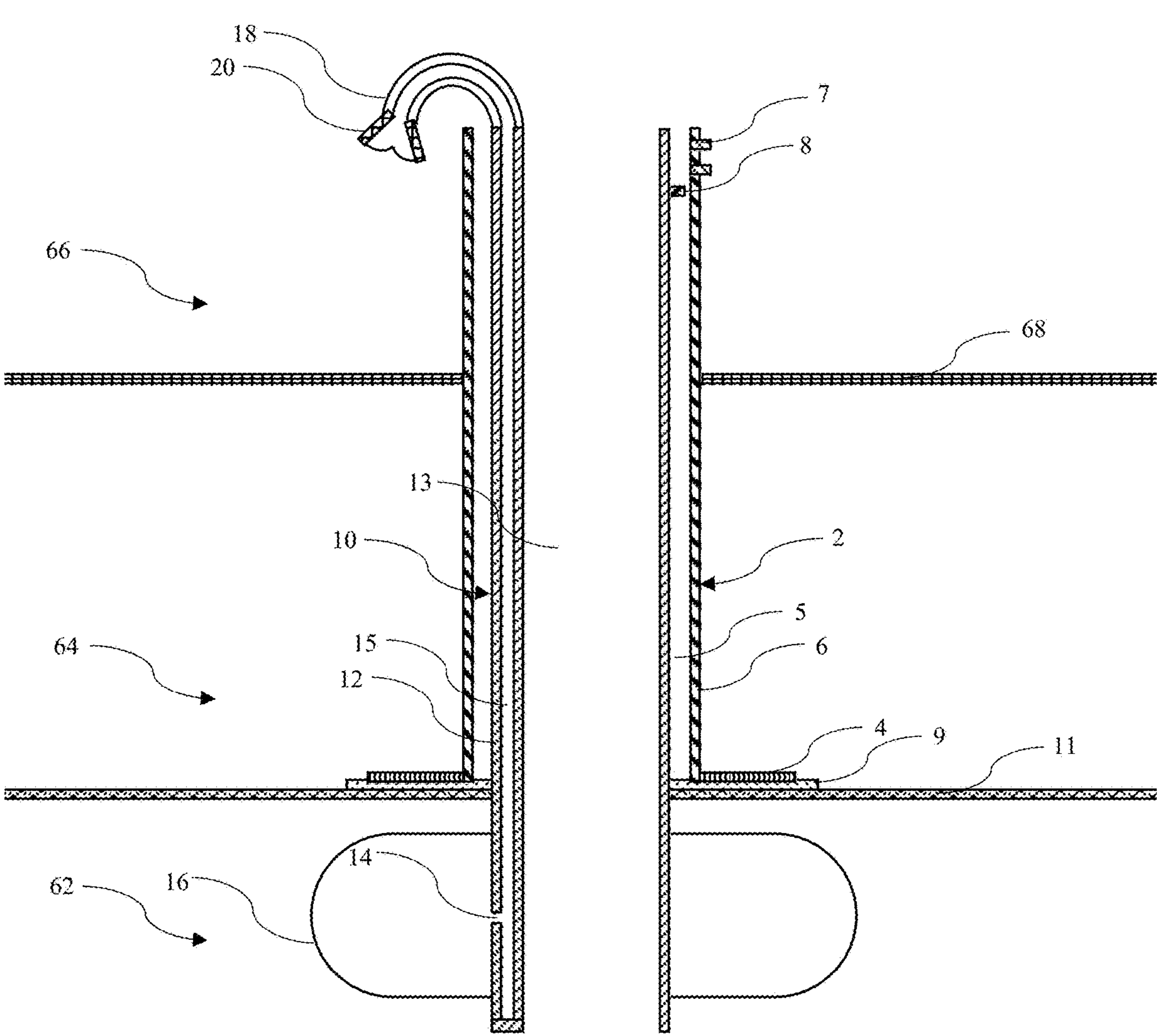
FIG. 7 depicts a sectional view of an exemplary embodiment of the invention involving activating the activatable tissue reinforcing element—in this embodiment, a balloon—in the distal space.

FIG. 7 shows the illustrative embodiment of the activation of the activatable tissue reinforcing element 16, which can be a balloon, following the advancement of the elongate assembly 10 sufficiently far into the distal space 62. Prior to the expansion of the activatable tissue reinforcing element 16, in the illustrative embodiment some contents from the distal space 62 can be aspirated through lumen 13 prior to expansion, in order to accommodate the increased volume occupied by the activatable tissue reinforcing element 16. In the illustrative embodiment, the elongate assembly 10 is then retracted in relation to outer housing 2 and securing mechanism 7 interacts with securing mechanism 8 in order to prevent the longitudinal translation of outer housing 2 and elongate assembly 10 in relation to one another, without requiring the user to hold them in such a position.

In another embodiment the activatable tissue reinforcing element 16 is activated without any prior aspiration. As noted previously, a variety of alternative embodiments can include elements that satisfy the function of the activatable tissue reinforcing element 16, including but not limited to a stent, cage (as shown in FIGS. 13 and 14), scissor-like device, or magnet, which can form a seal with the outer housing 2 from the distal space 62 following tissue wall 11 puncture such that in the event of adhesive 9 failure, no contents from the distal space 62 would escape into the proximal space 64. Also as mentioned previously, in other embodiments the securing of the outer housing 2 to the elongate assembly 10 can be accomplished in ways including but not limited to applying a clip to the elongate assembly 10, expanding a balloon on the proximal end of elongate member 10, closing a latch, or engaging a locking mechanism. Alternatively, the user can manually hold outer housing 2 and elongate assembly 10 in relation to one another.

Once again, FIG. 1 shows the illustrative embodiment in its working state, following the interaction of securing mechanism 7 with securing mechanism 8. In the illustrative embodiment suction tubing can be attached to connector 27 and allow for the aspiration of contents in the distal space 62. Connector 27 can be removed to allow an instrument to be inserted into the distal space 62 via lumen 13. Such an instrument can be used for a variety of purposes including but not limited to taking a biopsy of tissue, grasping tissue, or puncturing though additional septations. In its working state, such an apparatus can be used to aid in retracting and manipulating tissue wall 11, which can be useful for example in releasing a cyst or cyst-like structure that is adhered to other neighboring structures.

Figure 8:
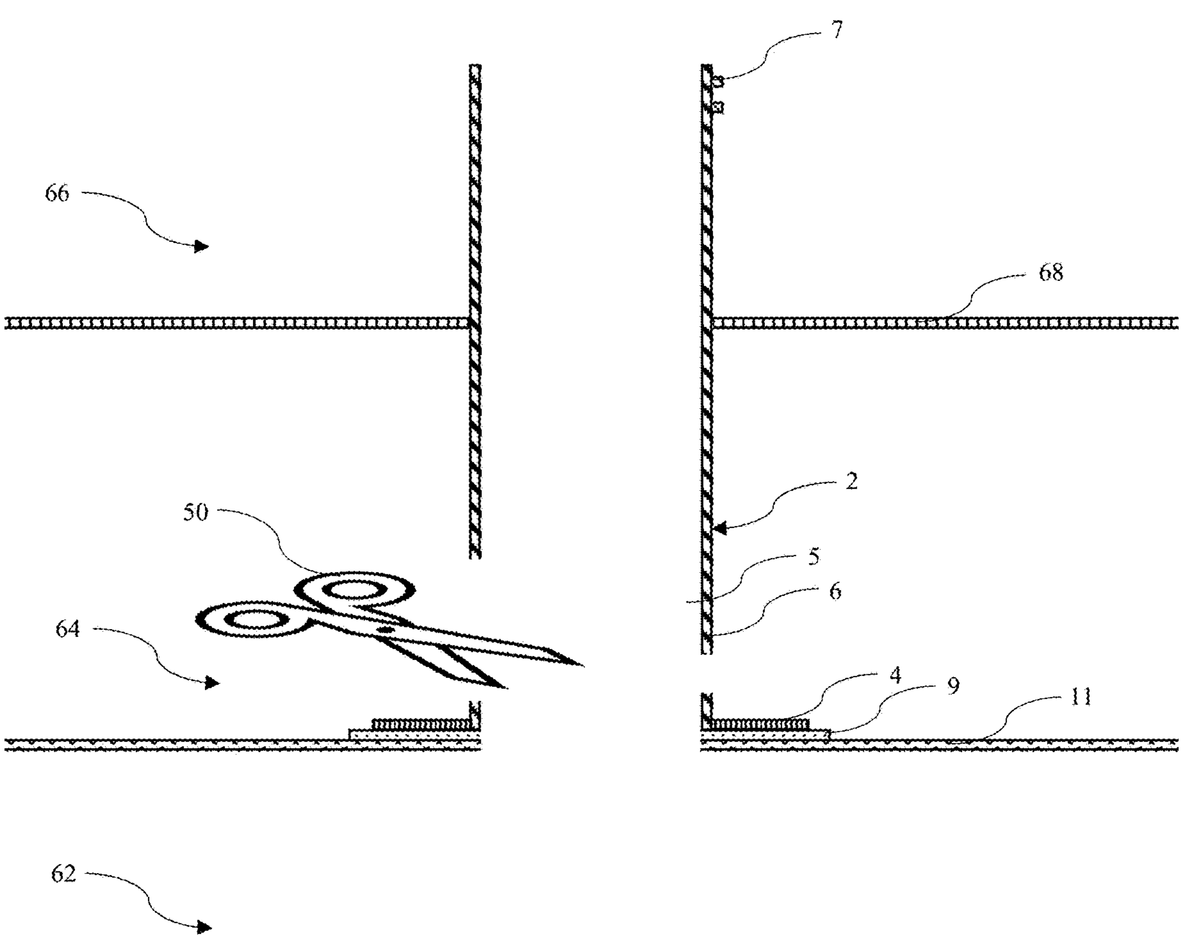
FIG. 8 depicts a sectional view of an exemplary embodiment of the invention involving severing a portion of the outer housing.

FIG. 8 shows an alternate embodiment where a cutting element 50 can be used to cut the tubular body 6 of the outer housing 2. Such an embodiment might be useful in the event that it is determined the contents within the distal space 62 are benign or have been sufficiency evacuated to no longer be viewed as a major spillage risk. In an alternate embodiment the tissue wall 11 can be cut in order to release a portion of the tissue wall and the outer housing 2. In another embodiment, the tubular body 6 can be melted and/or compressed to ablate lumen 5 prior to cutting, creating a seal that can be then cut through to prevent leakage of fluid from the lumen 5 proximally or distally. In another embodiment, the elongate assembly 10 can be cut in addition to the outer housing 2. In yet another embodiment, the distal portion of outer housing 2 can be biocompatible or biodegradable, and can be left attached to tissue wall 11 after its use has been performed.

Figure 9:
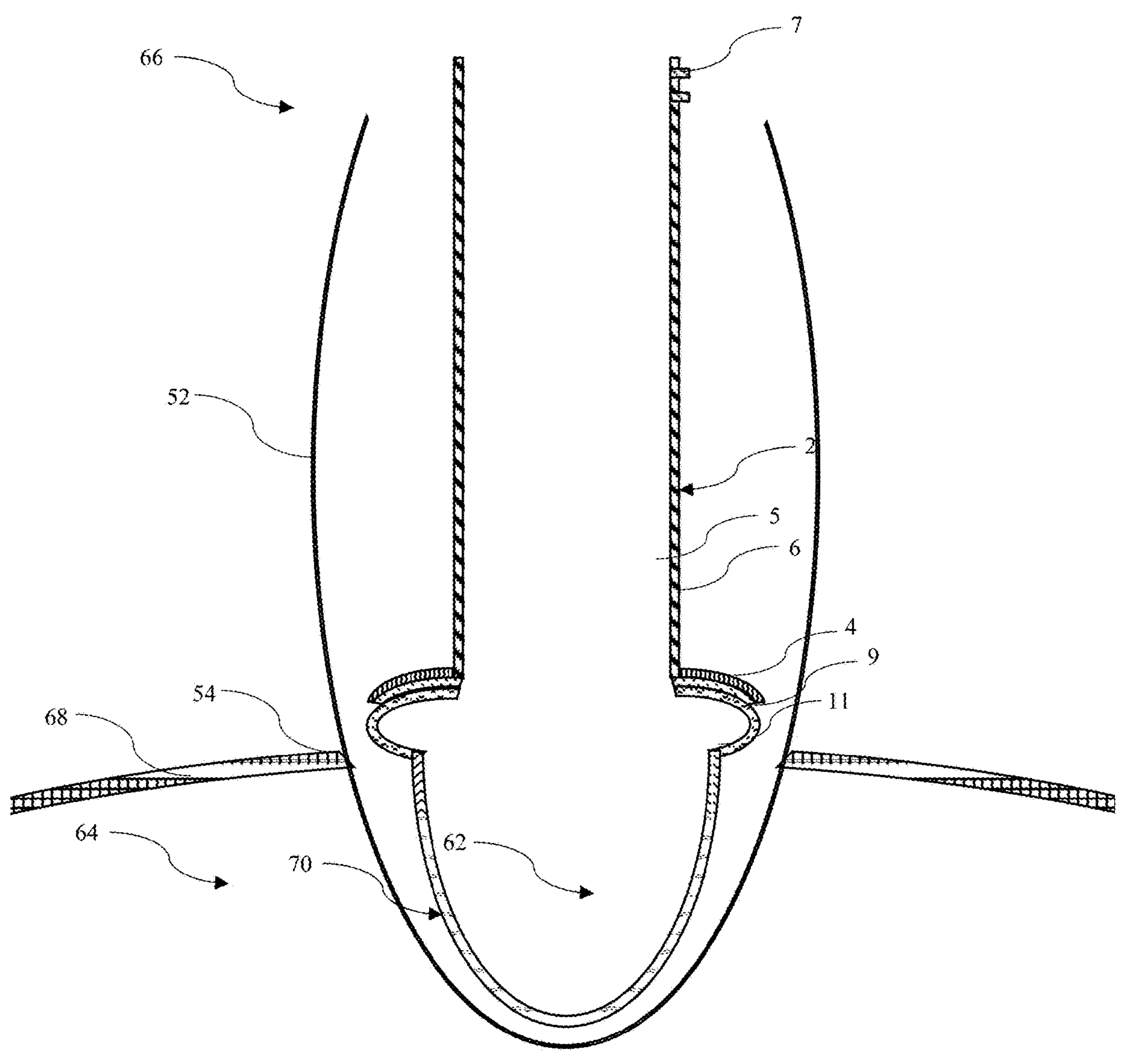
FIG. 9 depicts a sectional view of an exemplary embodiment of the invention involving removing the cyst or cyst-like structure from the incision opening.

FIG. 9 shows the illustrative embodiment of apparatus extraction to prevent the spillage of contents from a cyst or cyst-like structure 70, which is one exemplary, but not the only, application of the apparatus. If the tissue wall 11 forms the wall of the cyst or cyst-like structure 70 surrounding the distal space 62, the cyst or cyst-like structure 70 can be extracted while remaining adhered to tissue contacting element 4. After being mobilized from surrounding tissue and perhaps decompressed, the cyst or cyst-like structure 70 can be placed in an impermeable container, such as a plastic bag, and extracted through an incisional opening 54 of a body wall 68 with an impermeable container 52. The activatable tissue reinforcing element 16 can be inactivated and the elongate assembly 10 can or cannot be removed prior to fully removing the impermeable container 52. The impermeable container 52 acts as an added barrier to prevent spillage of the cyst or cyst-like structure 70 contents into the proximal space 64 during extraction through a potentially narrow incision opening 54.

In another embodiment, the cyst or cyst-like structure 70 can be extracted without first being surrounded by the impermeable container 52. Alternatively, the activatable tissue reinforcing element 16 can remain in its activated state during extraction. In another embodiment, before being mobilized completely from surrounding tissue, the cyst or cyst-like structure 70 can be partially or fully drawn thought the body wall 68 and out of the body into an outside space 66, to allow for some mobilization to occur in the outside space 66.

Figure 10:
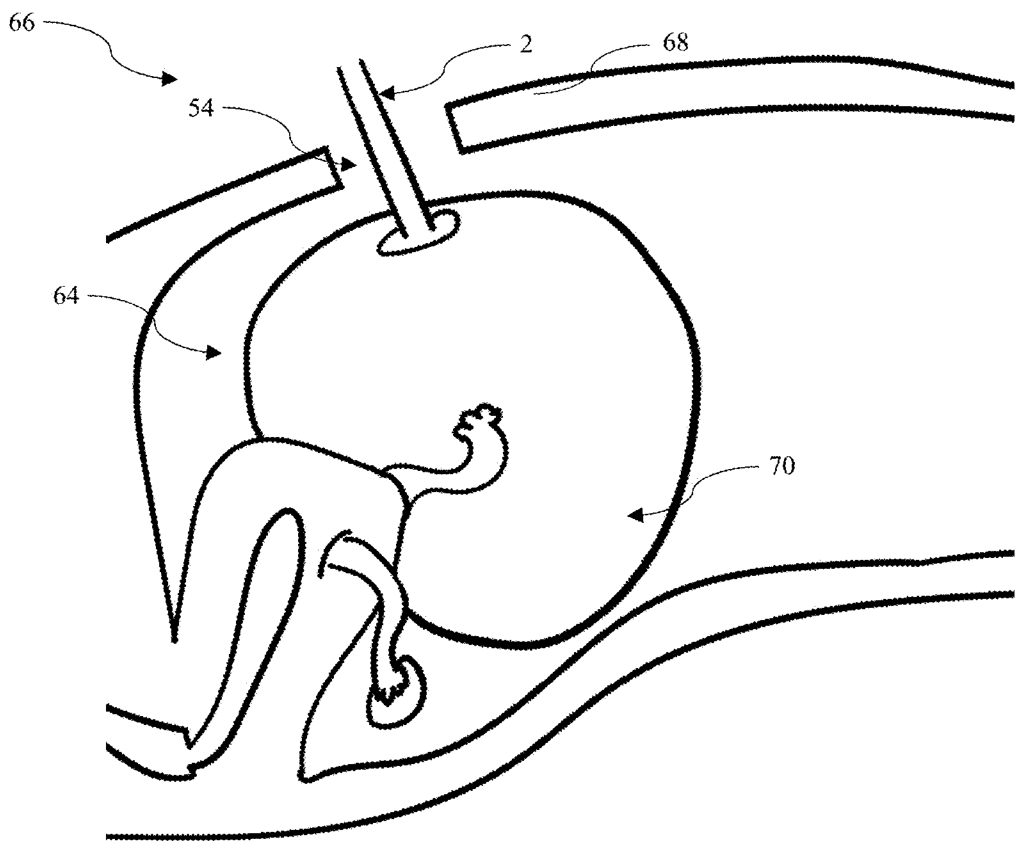
FIG. 10 depicts a compositional view of an exemplary embodiment of the invention involving open surgery.

FIG. 10 shows the apparatus being used in an exemplary application of cyst or cyst-like structure 70 extraction during a surgery with a laparotomy or mini-laparotomy incision. In an embodiment for this application, outer housing 2 passes through the incisional opening 54 and is adhered to the cyst or cyst-like structure 70. In some embodiments adhesive 9 can be applied directly to tissue contacting element 4 or the cyst or cyst-like structure 70 if the incisional opening 54 is sufficiently exposed and close to the cyst or cyst-like structure 70. In some embodiments for this application the length of outer housing 2 and/or the elongate assembly 10 can be less than what might be used in laparoscopic surgery for example, or they can be entirely flexible or mostly flexible. In an alternative embodiment outer housing 2 can have a sealing port at its proximal end though which elongate assembly 10 is inserted, such that fluid does not escape out of the outer housing 2 upon puncturing the cyst or cyst-like structure 70, which might otherwise exit outer housing 2 and drip back through the incisional opening 54 and into the proximal space 64, particularly if the elongate member 2 is shorter in length for an open surgery.

FIG. 11 shows the apparatus being used in an exemplary application of cyst or cyst-like structure 70 extraction during laparoscopic surgery. The apparatus can be manipulated inside the body in the proximal space 64 with the aid of a visualizing means 72, which can be for example a camera or optical lens. Such an application can be considered when the cyst or cyst-like structure 70 is for example difficult to access, covered by bowel or other structures, or connected to nearby structures with substantial adhesions, as such examples can increase the risk of inadvertent cyst or cyst-like structure 70 puncture with standard laparoscopic cyst or cyst-like structure mobilization techniques.

Various other embodiments will be clear to others with ordinary skill in the art from considerations of the present invention. The embodiments described here are merely for exemplary purposes only, with the true scope of the invention being outlined in the following claims.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

The invention claimed is:

1. An apparatus comprising:

an outer housing comprising a proximal portion, a distal portion and a lumen;

a tissue contacting element in operable contact with the distal portion of the outer housing and comprising a surface adapted to adhere to tissue forming a surface of a cyst or cyst-like structure;

an elongate assembly disposed within the outer housing comprising:

a proximal portion;

a distal portion;

an activatable tissue reinforcing element comprising an inflatable balloon;

an adhesive applicator disposed on the device to apply an adhesive to the tissue contacting element; and further comprising a securing mechanism that operably connects the outer housing to the elongate assembly wherein the tissue contacting element and the activatable tissue reinforcing element are disposed; in an arrangement on the apparatus such that:

the outer housing can be inserted in a patient in vivo so that the tissue contacting element is adhered to the outer surface tissue of the cyst or cyst-like structure;

the distal portion of the elongate assembly can be advanced through a puncture in the wall of the cyst or cyst-like structure;

the activatable tissue reinforcing element is disposed in the apparatus so as to such that the inflatable balloon when inflated provides a support for the tissue contacting element adhering to an outer surface of the cyst or cyst-like structure; and the apparatus can be disposed in vivo so that fluid can be removed from the cyst or cyst-like structure through the lumen, thereby inhibiting leakage of fluid from the cyst or cyst-like structure in vivo.

2. The apparatus of claim 1, wherein:

the lumen comprises a conduit for a gas or a liquid; and the conduit is operably connected to a port that introduces a gas or fluid into the balloon.

3. The apparatus of claim 1, further comprising a drying element disposed on the device to remove liquid from the outer surface tissue of a cyst or cyst-like structure prior to adhering the tissue contacting element to the outer surface tissue of a cyst or cyst-like structure.

4. A method for removing fluid from a cyst or cyst-like structure with the apparatus of claim 1, the method comprising:

introducing the outer housing comprising the lumen into an in vivo location in a patient having the cyst or cyst-like structure;

affixing the tissue contacting element to a tissue wall of the cyst or cyst-like structure using an adhesive;

puncturing the tissue wall of the cyst or cyst-like structure;

activating the activatable tissue reinforcing element; and removing the fluid from the cyst or cyst-like structure.

5. A method for puncturing a tissue with the apparatus of claim 1, the method comprising:

advancing the outer housing comprising a lumen through a proximal space;

affixing the distal portion of the outer housing to a tissue;

advancing the elongate assembly through the lumen;

puncturing the tissue from within the lumen of the device; and activating the activatable tissue reinforcing element from within a distal space so that the tissue is in operable contact with the activatable tissue reinforcing element, thereby reinforcing the fixation of the distal portion of the outer housing to the tissue.

6. The method according to claim 5, further comprising drying the tissue prior to fixing the distal portion of the outer housing to the tissue.

7. The method according to claim 5, wherein the distal portion of the outer housing is fixed to the tissue with an adhesive.

8. The method according to claim 5, further comprising adding and/or removing material into/out of the distal space through at least one lumen within the elongate assembly.

9. The method according to claim 5, further comprising inserting at least one surgical instrument through at least one lumen within the elongate assembly.

10. An apparatus for puncturing a tissue wall, the apparatus comprising:

an outer housing comprising a lumen having a proximal portion and a distal portion; an elongate assembly having a proximal portion, a distal portion, and an activatable tissue reinforcing element, wherein the activatable tissue reinforcing element comprises an inflatable balloon; an adhesive applicator disposed on the device to apply an adhesive to the tissue contacting element; and further comprising a securing mechanism disposed in the apparatus so as to fix the outer housing and the elongate assembly in relation to each other;

wherein the elements are disposed in a three-dimensional arrangement on the apparatus such that:

the outer housing can be advanced through a proximal space;

the distal end of the outer housing can be fixed to a tissue wall;

the elongate assembly can be advanced through the lumen and is distal portion into a distal space through a puncture in the tissue wall; and the activatable tissue reinforcing element can be activated within the distal space such that the fixation of the outer housing to the tissue wall is reinforced by the inflatable balloon when the inflatable balloon is inflated.

11. The apparatus according to claim 10, further comprising a drying element disposed in the apparatus so as to dry the tissue wall prior to fixing the distal portion of the outer housing to the tissue wall.

12. The apparatus according to claim 10, further comprising an adhesive applicator disposed in the apparatus so as to apply adhesive for adhering the distal portion of the outer housing to the tissue wall.

13. The apparatus according to claim 10, further comprising a piercing member disposed in the apparatus so as to form a puncture in the tissue wall from within the lumen.

14. The apparatus according to claim 10, further comprising a suction element attachable to the elongate assembly and coupled the apparatus so as to remove material from the distal space.

* * * * *